United States Patent
Gonzalez et al.

(10) Patent No.: US 6,517,816 B1
(45) Date of Patent: Feb. 11, 2003

(54) SUNSCREEN EMULSION COMPOSITION AND METHOD OF USE

(75) Inventors: Anthony D. Gonzalez, Waldwick, NJ (US); Andrew H. Pechko, Ridgewood, NJ (US); Helen Wang, Suffern, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/032,847

(22) Filed: Dec. 26, 2001

(51) Int. Cl.[7] ............................. A61K 7/42; A61K 7/44; A61K 31/74; A61K 7/00
(52) U.S. Cl. ................. 424/59; 427/78.02; 427/78.08; 427/400; 427/401; 427/60; 514/937; 514/938; 514/939
(58) Field of Search ................................ 424/59, 78.02, 424/78.08, 400, 401; 514/937, 938, 939

(56) References Cited

U.S. PATENT DOCUMENTS

| | | |
|---|---|---|
| 4,015,009 A | 3/1977 | Chakrin et al. |
| 4,024,106 A | 5/1977 | Mader |
| 4,455,295 A | 6/1984 | Hopp et al. |
| 4,613,499 A | 9/1986 | Conner |
| 4,710,373 A | 12/1987 | Nakamura et al. |
| 4,863,963 A | 9/1989 | Nakai et al. |
| 5,160,731 A | 11/1992 | Sabatelli et al. |
| 5,338,539 A | 8/1994 | Giuseppe |
| 5,426,210 A | 6/1995 | Kato et al. |
| 5,783,173 A | 7/1998 | Bonda et al. |
| 5,917,088 A | 6/1999 | Philippe et al. |

*Primary Examiner*—Shelley A. Dodson
(74) *Attorney, Agent, or Firm*—Ohlandt, Greeley, Ruggiero & Perle, LLP

(57) ABSTRACT

There is provided a sunscreen emulsion composition. The composition has an inner discontinuous phase and an outer continuous phase. The inner discontinuous phase and/or outer continuous phase has a sunscreen active therein. The inner discontinuous phase is generally dispersed in the outer continuous phase and is in the form of discrete droplets having a multimodal droplet size distribution. There is also provided a method of protecting skin from overexposure to the sun in which the above composition is applied topically to the skin. There is also provided a method of enhancing the performance of a sunscreen emulsion by forming the inner discontinuous phase as a multiplicity of droplets having a multimodal droplet size distribution. There is also provided a method of preparing an emulsifier-free sunscreen composition.

37 Claims, 3 Drawing Sheets

SUNSCREEN EMULSION COMPOSITION AND METHOD OF USE

BACKGROUND OF THE INVENTION

1. Field of the Invention

The present invention relates to sunscreen emulsion compositions that provide improved sunscreen protection to skin. The present invention also relates to a method of improving the sunscreen protection factor ("SPF") of a sunscreen emulsion composition. Additionally, the present invention also relates to a method of providing a desired SPF to an emulsion composition using less sunscreen active(s).

2. Description of the Prior Art

Sunscreen compositions are available commercially in the form of emulsions with hydrophobic organic sunscreen actives in the inner discontinuous phase. Such emulsions are shown, by way of example, in U.S. Pat. Nos. 4,015,009; 4,024,106; 4,455,295; 4,613,499; 4,710,373; 4,863,963; 5,160,731; 5,338,539; 5,426,210; 5,783,173; and 5,917,088.

Heretofore, it has been traditionally accepted by those skilled in the art that highly stable emulsions (i.e., with small uniform droplet size) were necessary to produce sunscreen emulsions with high SPF. It has been observed that such stable emulsions require the use of relatively high levels of emulsifying agents, film formers and sunscreen actives. The prior art problem to be addressed is how to provide improved sunscreen protection products, preferably maximum sunscreen protection products, with a minimum amount of sunscreen active.

Thus, it is desirable to have a stable sunscreen composition in emulsion form that provides enhanced sunscreen protection with a lesser amount of a sunscreen active than previously possible.

SUMMARY OF THE INVENTION

It is an object of the present invention to provide a sunscreen emulsion composition that provides enhanced sunscreen protection.

It is another object of the present invention to provide a sunscreen emulsion composition that provides a given degree of sunscreen protection with a lesser amount of sunscreen active than previously possible.

It is another object of the present invention to provide a method of protecting skin from ultraviolet radiation and the damage (e.g., wrinkles, sunburn) associated therewith.

These and other objects and advantages of the present invention are provided in the present sunscreen composition by reducing the steric stability of a sunscreen emulsion compositions, i.e., by preparing a meta-stable emulsion. The emulsion has an inner discontinuous phase and an outer continuous phase. The inner discontinuous phase and/or outer continuous phase has at least one sunscreen active therein. The inner discontinuous phase is generally dispersed within the outer continuous phase in the form of discrete droplets having a multimodal droplet size distribution.

DETAILED DESCRIPTION OF THE INVENTION

As stated above, the prior art teaches that, in order to obtain efficacious sunscreen protection from a sunscreen emulsion composition, the emulsion must be stable. This inherently means that the droplet size distribution throughout the emulsion is uniform/homogenous. By maintaining such uniform droplet size distribution, the droplets are less likely to come together and cause the internal and external phases of the emulsion to separate and become unstable. To maintain this uniform droplet size distribution, a relatively high degree of emulsifying agent is required, typically 10 percentage by weight or weight percent (wt %) or more based on the total weight of the inner phase components. By lowering the amount of emulsifying agent, the droplet size distribution becomes increasingly heterogeneous and causes the emulsion to become meta-stable and, ultimately, unstable if a very low amount or no emulsifying agent is used. It has, heretofore, been the common understanding that, as the stability of a sunscreen emulsion composition decreases, the sunscreen performance of such a composition similarly decreases. Contrary to the teachings of the prior art, it has now been unexpectedly and surprisingly found that sunscreen emulsion compositions with reduced steric stability (i.e., emulsions that have a heterogeneous/multi-modal droplet size distribution) provide better sunscreen performance (e.g., a higher SPF) than prior art stable emulsions (i.e., emulsions that have uniform/unimodal droplet size distribution) having equal amounts of the same sunscreen active. Alternatively, sunscreen emulsions with reduced steric stability (i.e., meta-stable emulsions) can impart the same SPF values as sterically stable sunscreen emulsions, but with lesser amounts of sunscreen active(s).

As used herein, the term "SPF enhancement" includes, as compared to prior art sunscreen compositions, (1) increasing SPF levels of the composition without increasing the concentration of sunscreen active, and (2) maintaining the same SPF levels with lower concentrations of sunscreen active. The main requirement for SPF enhancement is that the emulsion must be stable, but with heterogeneous droplets.

Figure 1:
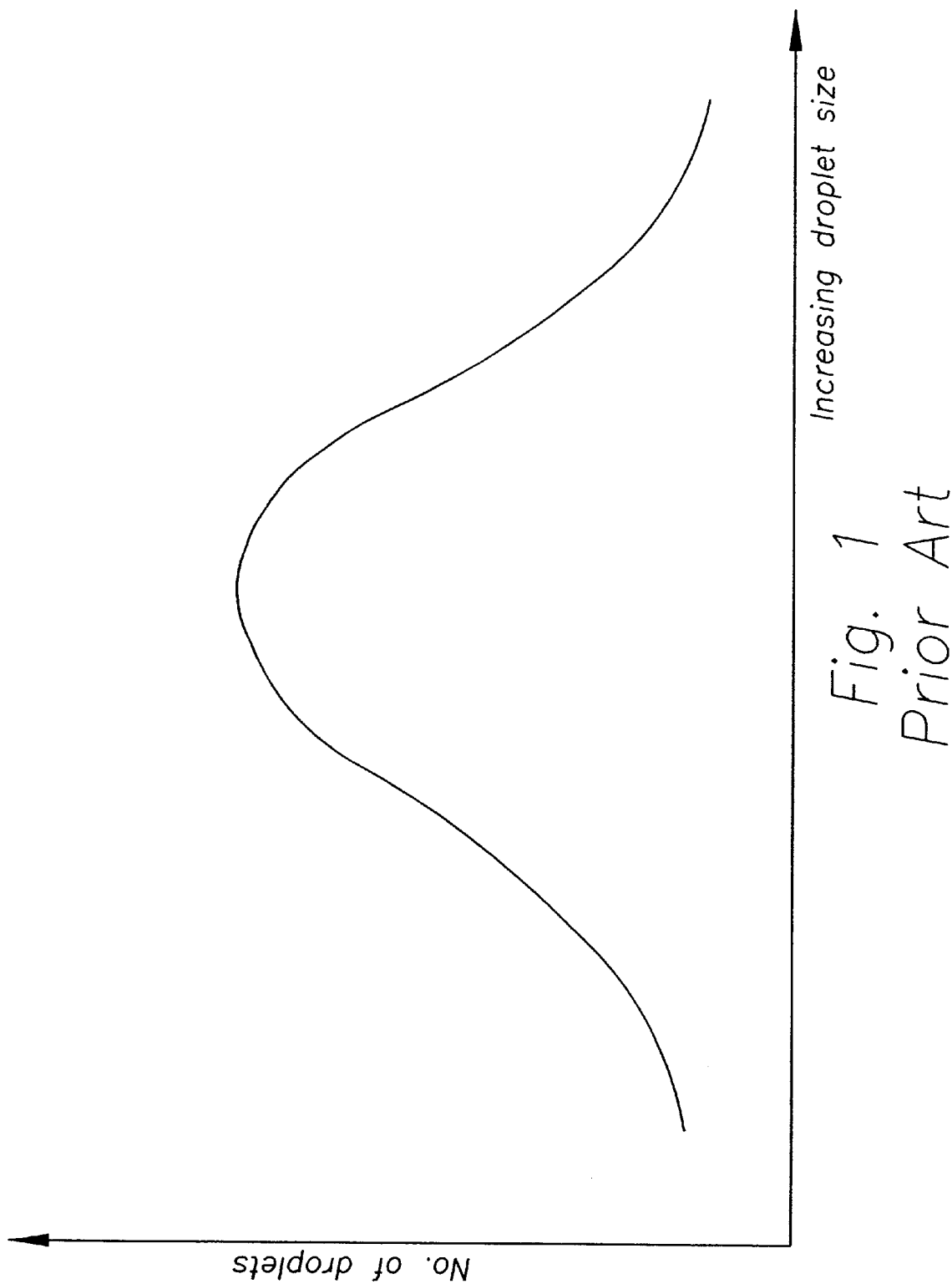
FIG. 1 illustrates a representation of a unimodal (i.e., uniform/homogeneous) droplet size distribution of a conventional (i.e., prior art) emulsion.

In the present invention, a meta-stable emulsion can be prepared by simply reducing the amount of traditional emulsifying agent used to emulsify the inner and outer phases of the emulsion. Alternatively, the traditional emulsifying agents can be replaced altogether with certain co-solvents, as will be described herein. Similarly, an emulsion composition can be converted from stable to meta-stable by raising the concentration of the inner phase of the emulsion and/or by decreasing the external phase of the emulsion. In either case, the inner and outer phases of the emulsion will be emulsified only to a point where the emulsion is meta-stable. In other words, the emulsion will not have the uniform droplet size distribution associated with highly stable emulsions. This type of distribution is referenced to as unimodal and is shown in FIG. 1. Rather, the meta-stable emulsion of the present invention will inherently have a heterogeneous droplet size distribution (that accounts for its meta-stability). This type of distribution is referred to as multimodal (shown in FIGS. 2 and 3) because the droplets are present in the emulsion in at least two different size distribution ranges, as would be easily determinable by viewing the emulsion under a light microscope or by laser particle size analyzer.

A composition that has two different droplet size ranges may also be referred to as "bimodal". A composition with three different ranges may also be referred to as "trimodal." A composition with four or more different ranges or in a wide range of droplet sizes may also be referred to as "polymodal."

Figure 2:
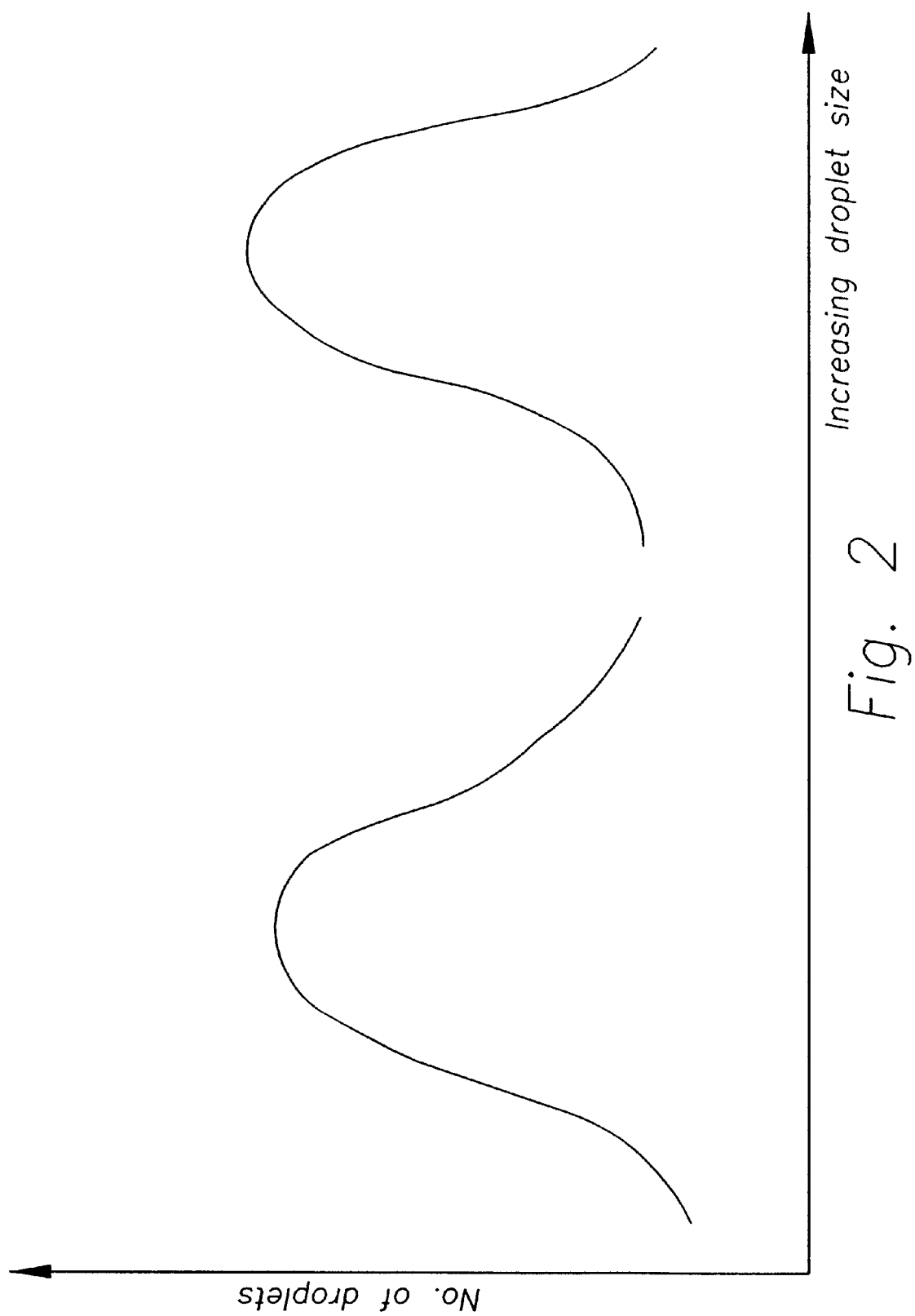
FIG. 2 illustrates a representation of a meta-stable emulsion of the present invention having a bimodal (i.e., non-uniform/heterogeneous) droplet size distribution range.

A bimodal droplet size distribution is represented in FIG. 2. As is appreciated, there are two discrete droplet size ranges. In other words, a majority of the droplet sizes fall within the two discrete ranges as represented by the area under the curves. A non-limiting example of such a bimodal emulsion of the present invention includes a first droplet size range about 4 to about 8.5 microns, and a second droplet size range about 1 to about 2 microns.

Figure 3:
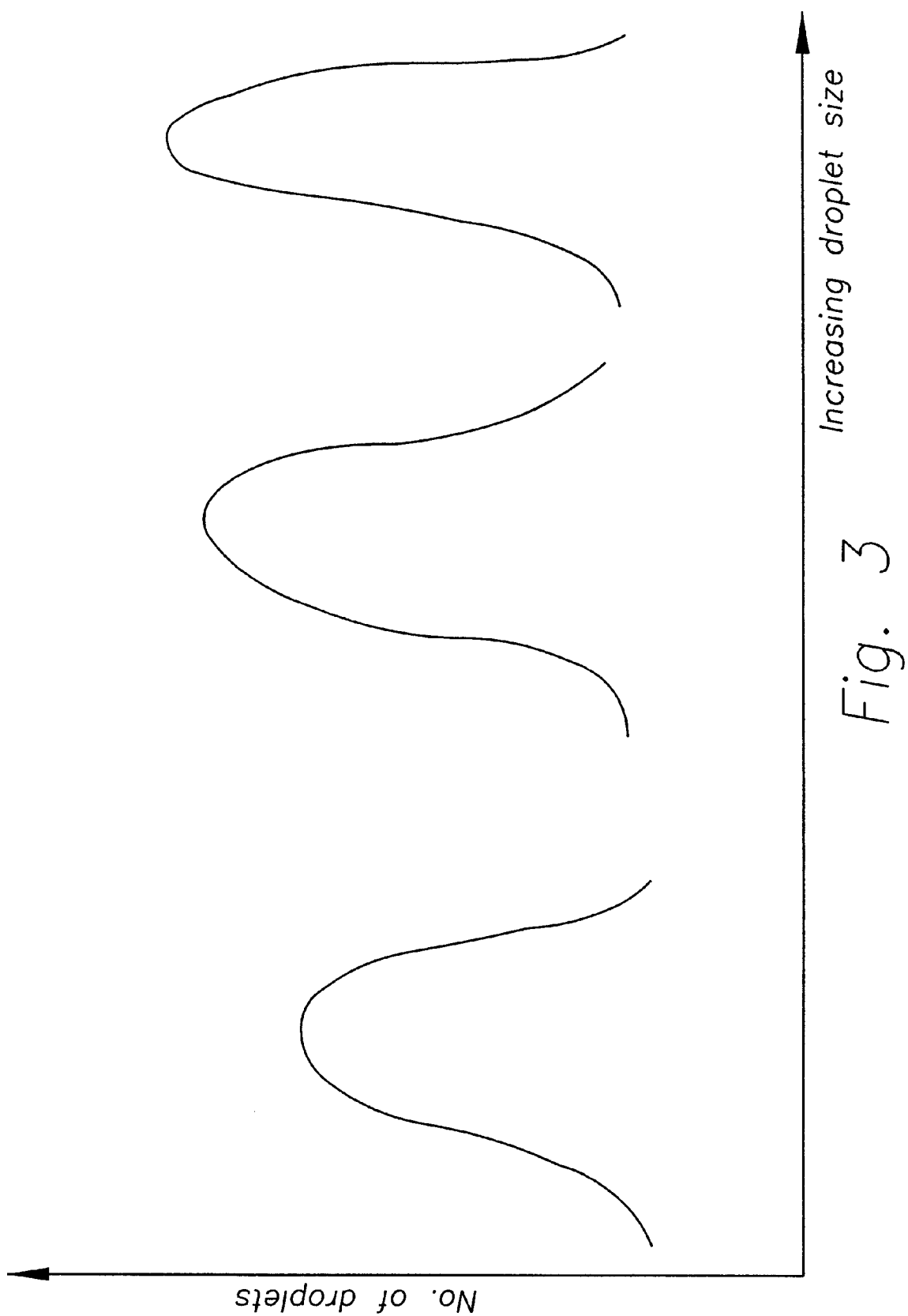
FIG. 3 illustrates a representation of a meta-stable emulsion of the present invention having a trimodal (i.e., non-uniform/heterogeneous) droplet size distribution range.

A trimodal droplet size distribution is represented in FIG. 3. As is appreciated, there are three discrete droplet size ranges. In other words, a majority of the droplet sizes fall in the three discrete ranges as represented by the area under the curves. A non-limiting example of such a trimodal emulsion of the present invention has a first droplet size range about 50 to about 120 microns, a second droplet size range about 20 to about 35 microns, and a third droplet size range about 7 to about 10 microns.

As employed herein, "droplet size" refers to droplet diameter. Droplet size is determined via microscopy using image analysis software. Droplet size may also be determined using a laser particle size analyzer.

With respect to the present invention, the droplet size and droplet size ranges are not to be limited to a specific size or range of sizes. Rather, it is more important that the sunscreen emulsion have at least two discrete droplet size ranges. Preferably, at least about 50 wt % of the droplets fall within the discrete droplet size ranges based upon the total weight of droplets. Still more preferably, at least about 70 wt % to about 90 wt % of the droplets fall within the discrete droplet size ranges based upon the total weight of droplets.

The composition may preferably take the form of an oil-in-water emulsion, a water-in-oil emulsion, a water-in-silicone emulsion, a silicone-in-water emulsion, oil-in-oil emulsion, polyol-in-silicone emulsion, a multiple emulsion, and an inverse emulsion. An oil-in-water emulsion is more preferred.

The present composition has a sunscreen agent in either the inner discontinuous phase or outer continuous phase of the emulsion. The sunscreen may be organic or inorganic and water-soluble or oil-soluble. Such useful sunscreen actives include those for UVA and UVB protection (290 to 400 nanometer solar radiation). Such useful actives include, but are not limited to, oxybenzone, sulisobenzone, dioxybenzone, menthyl anthranilate, para aminobenzoic acid (PABA), octyl methoxycinnamate, octocrylene, drometrizole trisiloxane, octyl salicylate, homomenthyl salicylate, octyl dimethyl PABA, TEA salicylate, butylmethoxy dibenzoylmethane (avobenzone), 4-methyl benzylidene camphor, 3-benzylidene camphor, benzylidene camphor sulfonic acid, octyl triazone, terephthalydiene dicamphor sulfonic acid, ethyl PABA, hydroxy methylphenyl benzotriazole, methylene bis-benzotriazoyltetramethylbutylphenol, diethylhexyl-2,6-naphthalate, di-t-butyl hydroxybenzylidene camphor, bis-ethylhexyloxyphenol methoxyphenol triazine, titanium dioxide, zinc oxide, or any combinations of the foregoing. Other useful sunscreen actives include those disclosed in U.S. Pat. No. 5,000,937, which is incorporated herein by reference.

The sunscreen active is present at up to about 70 wt %, preferably about 0.05 wt % to about 50 wt %, and most preferably about 0.5 wt % to about 30 wt %, based on the total weight of the composition. The amount of sunscreen active employed will depend on the level of protection desired. Although not to be construed as limiting, compositions will typically range in their level of sunscreen protection factor (SPF) from about 2 to about 70. Preferably, the present invention is used to provide a composition having a sunscreen protection factor at least about 2, more preferably at least about 8, and most preferably about 15 to about 30.

The composition has an aqueous phase that is about 10 wt % to about 90 wt %, preferably about 20 wt % to about 80 wt %, and most preferably about 25 wt % to about 75 wt % water, based on the total weight of the composition.

The present composition may include any vehicle known in the art as useful in formulating emulsions. Suitable vehicles include, but are not limited to, water; one or more vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones and polysiloxanes; hydrocarbon oils such as mineral oil, petrolatum, isoeicosane and polyisobutene; polyols such as propylene glycol, glycerin, butylene glycol, pentylene glycol and hexylene glycol; or any combinations of the foregoing.

The composition may have an emulsifier present in a limited amount effective to provide and maintain a heterogeneous, meta-stable dispersion of the inner discontinuous phase in the outer continuous phase, in which the heterogeneous droplets are in multimodal droplet size ranges. Preferably, the emulsifier will be present in an amount up to about 5 wt %, more preferably up to about 2 wt %, even more preferably up to about 1%, and most preferably up to about 0.5 wt %, based upon the total weight of the inner phase components/ingredients.

Of course, the level of emulsifier used can be modified by those skilled in the art, especially when using more powerful emulsifiers such as polymerics and/or cosolvents such as polyols. The excipients of the composition can be selected to alter the required emulsifier level as well. For example, including a more polar oil, such as isopropylmyristate, instead of a nonpolar oil, such as a hydrocarbon oil, allows the amount of emulsifier required to maintain a meta-stable emulsion to be decreased.

Emulsifiers that can be used in the present compositions include, but are not limited to, one or more of the following: sorbitan esters such as sorbitan monooleate and sorbitan monostearate; polyglycerol esters and glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; polyglyceryl-3-diisostearate; polyglyceryl-3-distearate; PEG-30 dipolyhydroxystearate; quaternary ammonium compounds; dimethicone copolyol; cetyl dimethicone copolyol; lecithin and its components; alkyl polyglucosides; acrylates/$C_{10}$–$C_{30}$ alkyl acrylate copolymers; or any combinations thereof, or any other component that can sufficiently reduce the surface tension between phases to allow for the formation of discrete inner phase droplets. Additional useful emulsifiers and co-emulsifiers are provided in U.S. Pat. No. 5,162,378 (column 4) and U.S. Pat. No. 5,344,665 (Table 1), which are incorporated herein by reference.

The meta-stable emulsions of the present invention may be made substantially free of traditional emulsifying agents and still provide SPF enhancement. When the meta-stable emulsion is substantially emulsifier-free, it is preferred that the emulsion includes at least one co-solvent with low surface activity (i.e., can reduce surface tension to help emulsify the emulsion phases, but without producing a fully stable emulsion). The co-solvents that can be used in the present composition include, but are not limited to, one or more polyols, such as butylene glycol, ethylene glycol, propylene glycol and hexylene glycol; esters such as octyl palmitate, isopropyl myristate and isopropyl palmitate; ethers such as dicapryl ether and dimethyl isosorbide; ethoxylated esters; propoxylated esters; propoxylated alcohols; and alkoxylated alcohols such as polyethylene glycol. Preferably, the co-solvent is a polyethylene glycol. Suitable non-limiting examples of polyethylene glycols useful in the present invention include polyethylene glycol 1450 and polyethylene glycol 300.

It is preferred that the ratio of co-solvent to sunscreen is about 0.5:1 to about 10:1, more preferably about 0.5:1 to about 5:1, and optimally at about 1:1.

When preparing such an emulsifier-free composition, it is most preferable to mix the sunscreen and co-solvent together before any other ingredients are added to the sunscreen. As used herein, the term "substantially emulsifier-free" means less than about 1 wt % emulsifying agent based on the total weight of the composition.

The present invention may also incorporate emulsion stabilizers to impede the coalescence of the internal phase droplets. Such stabilizers may include, but are not limited to, polymers such as carbomer, cellulosics (organo-modified and otherwise), clays such as bentonite and its derivative, suspending powders such as silica, and polymethylmethacrylate. In the case of inverse emulsions, salts such as magnesium sulfate heptahydrate may also be used as emulsion stabilizers. Lowering the concentration of emulsion stabilizers in a stable cosmetic emulsion will also contribute to converting such stable emulsion to a meta-emulsion.

The present composition may optionally include one or more of the following ingredients: anesthetics; anti-allergenics, antifungals, antimicrobials, anti-inflammatories, antiseptics, chelating agents, botanical extracts, colorants, depigmenting agents, emollients, exfollients, film formers, fragrances, humectants, insect repellents, lubricants, moisturizers, pharmaceutical agents, preservatives, skin protectants, skin penetration enhancers, stabilizers, surfactants, thickeners, viscosity modifiers, vitamins, or any combinations thereof.

While the inventors do not wish to be bound by any one theory, it is believed that the meta-stable emulsions of the present invention may provide SPF enhancement by forming a more uniform film, thus making the addition of a film former unnecessary. However, conventional film formers may still be added to the present invention, if desired.

The composition can be made into any suitable product form. Such product forms include, but are not limited to, a cream, a lotion, a gel, a solution, and an aerosol or pump spray. In addition, the composition may be incorporated into a stick, towelette, or patch.

The composition may be formulated in any manner known in the art for forming an emulsion having a sunscreen. Typically, the aqueous phase and the oil phase will be separately formulated and subsequently mixed. The main requirement for SPF enhancement under the present invention is that the emulsion be meta-stable. The stability of an emulsion is based principally on a physical observation test. Basically, the emulsion is put through 3 freeze/thaw cycles in which the temperatures are accelerated between a low of about 40° F. to a high of about 120° F. The emulsion is then observed at 4 week and 8 week intervals. The product is deemed stable if no separation of the phases occurs, and the product maintains physical integrity, such as viscosity and pH parameters.

EXAMPLE

A stable, water-in-oil emulsion (Composition 1) was prepared. Using a light microscope with image analysis software, the droplet size distribution was determined to be uniform, as the droplets did not vary significantly in size.

Composition 2 was prepared by modifying Composition 1 to make it meta-stable (the invention). The droplet size distribution was determined to be heterogeneous.

Compositions 1 and 2 are set forth in the following Table 1:

TABLE 1

| Ingredient | Wt % Composition 1 | Wt % Composition 2 |
| --- | --- | --- |
| Water | 16.37 | 25.47 |
| Oil phase (e.g., cyclomethicone, etc.) | 40 | 33.4 |
| Emulsion stabilizer (e.g., magnesium sulfate salt) | 1 | 0.5 |
| Emulsifier (e.g. dimethicone copolyol) | 0.08 | 0.08 |
| Sunscreen (e.g. octylmethoxycinnamate, octyl salicylate, zinc oxide, etc. | 30 | 30 |
| Film former (e.g., timethyl siloxysilicate) | 2.5 | 1.5 |
| Dispersant (e.g. cetyl dimethicone copolyol, etc.) | 0.85 | 0.85 |
| Preservative (e.g., methyl paraben, etc.) | 1.2 | 1.2 |
| Co-solvent (e.g., butylene glycol, etc. | 2 | 2 |
| Feel modifier (e.g., polymethyl methoxylate) | 6 | 6 |

Both compositions were tested for SPF. Composition 1 was found to have an SPF of about 31. Composition 2 was found to have an SPF of about 53. This result was surprising and unexpected, especially in light of the fact that several of the modifications that were made would typically be expected to decrease the SPF demonstrated by Composition 1. For example, the internal (water) phase was increased, the emulsion stabilizer was decreased by 50%, and the external (oil) phase was decreased. The concentration and type of sunscreen active were maintained the same. Although the foregoing modifications would be expected to decrease the resulting SPF due to the meta-stability of the emulsion, Composition 2 (the invention) surprisingly provided an SPF potentiation over 67% from the SPF demonstrated by Composition 1.

As is evident from the above example, it is highly surprising that a sunscreen emulsion that is less than fully stable (i.e., meta-stable) provides enhanced sunscreen protection as compared to a similar, fully stable emulsion. It was not at all expected that the meta-stability of the emulsion would function to potentiate the activity of the sunscreen. The exact opposite would have been expected.

It should be understood that the foregoing description is only illustrative of the present invention. Various alternatives and modifications can be made by those skilled in the art without departing from the present invention. Accordingly, the present invention is intended to embrace all such alternatives, modifications and variances that fall within the scope of the appended claims.

What is claimed is:

1. An emulsion composition, comprising:
   at least one sunscreen active;
   an inner discontinuous phase; and
   an outer continuous phase,
   wherein the composition is meta-stable.

2. The composition of claim 1, wherein the inner discontinuous phase is a plurality of droplets having a multimodal droplet size distribution.

3. The composition of claim 1, wherein the composition takes the form of an oil-in-water emulsion.

4. The composition of claim 1, wherein the composition takes the form of an emulsion selected from the group consisting of an oil-in-water emulsion, a water-in-oil emulsion, a water-in-silicone emulsion, a silicone-in-water emulsion, oil-in-oil emulsion, polyol-in-silicone emulsion, a multiple emulsion, and an inverse emulsion.

5. The composition of claim 1, wherein the emulsion has a heterogeneous droplet size distribution.

6. The composition of claim 1, wherein the droplet size distribution is bimodal.

7. The composition of claim 1, wherein the droplet size distribution is trimodal.

8. The composition of claim 1, wherein the droplet size distribution is polymodal.

9. The composition of claim 1, wherein the sunscreen active is selected from the group consisting of oxybenzone, sulisobenzone, dioxybenzone, menthyl anthranilate, para aminobenzoic acid (PABA), octyl methoxycinnamate, octocrylene, drometrizole trisiloxane, octyl salicylate, homomenthyl salicylate, octyl dimethyl PABA, TEA salicylate, butylmethoxy dibenzoylmethane (avobenzone), 4-methyl benzylidene camphor, 3-benzylidene camphor, benzylidene camphor sulfonic acid, octyl triazone, terephthalydiene dicamphor sulfonic acid, ethyl PABA, hydroxy methylphenyl benzotriazole, methylene bis-benzotriazoyltetramethylbutylphenol, diethylhexyl-2,6-naphthalate, di-t-butyl hydroxybenzylidene camphor, bis-ethylhexyloxyphenol methoxyphenol triazine, titanium dioxide, zinc oxide, and any combinations thereof.

10. The composition of claim 1, wherein the at least one sunscreen active is present at up to about 70 wt % based on the total weight of the composition.

11. The composition of claim 1, wherein the at least one sunscreen active is present at about 0.05 wt % to about 50 wt % based on the total weight of the composition.

12. The composition of claim 1, wherein the at least one sunscreen active is present at about 0.5 wt % to about 30 wt % based on the total weight of the composition.

13. The composition of claim 1, wherein the composition exhibits an SPF about 2 to about 70.

14. The composition of claim 1, wherein the composition exhibits an SPF about 15 to about 30.

15. The composition of claim 1, wherein the composition is substantially free of an emulsifying agent.

16. The composition of claim 15, wherein the emulsifier is present in an amount less than about 1 wt % based on the total weight of the composition.

17. The composition of claim 16, further comprising a co-solvent.

18. The composition of claim 17, wherein the co-solvent is selected from the group consisting of one or more polyols, esters, ethers, propoxylated esters, propoxylated alcohols, and alkoxylated alcohols, and any combinations thereof.

19. The composition of claim 17, wherein the co-solvent is polyethylene glycol.

20. The composition of claim 1, wherein the composition is in a product form selected from the group consisting of a cream, a lotion, a gel, a solution, an aerosol spray, and a pump spray.

21. The composition of claim 1, wherein the composition is incorporated into a product form selected from the group consisting of a stick, a towelette, and a patch.

22. The composition of claim 1, further comprising an ingredient selected from the group consisting of one or more anesthetics, anti-allergenics, antifungals, antimicrobials, anti-inflammatories, antiseptics, botanical extracts, chelating agents, colorants, depigmenting agents, emollients, exfollients, film formers, fragrances, humectants, insect repellents, lubricants, moisturizers, pharmaceutical agents, preservatives, skin protectants, skin penetration enhancers, stabilizers, surfactants, thickeners, viscosity modifiers, vitamins, and any combinations thereof.

23. The composition of claim 1, further comprising up to about 5% of an emulsifier based on the total weight of the inner phase.

24. The composition of claim 1, further comprising up to about 2% of an emulsifier based on the total weight of the inner phase.

25. The composition of claim 1, further comprising up to about 0.5% of an emulsifier based on the total weight of the inner phase.

26. The composition of claim 1, further comprising an insect repellent.

27. A method of protecting skin from exposure to the sun, comprising applying topically to the skin the emulsion composition according to claim 1.

28. A method of enhancing the performance of a sunscreen composition, comprising forming an emulsion having an inner discontinuous phase and an outer continuous phase, adding a sunscreen active to the emulsion, and rendering the emulsion meta-stable.

29. The method of claim 28, wherein the emulsion has a plurality of droplets of multimodal droplet size distribution.

30. The method of claim 28, further comprising adding up to about 5% of an emulsifier, based on the total weight of the inner phase.

31. The method of claim 28, further comprising adding up to about 2% of an emulsifier, based on the total weight of the inner phase.

32. The method of claim 28, further comprising adding up to about 0.5% of an emulsifier, based on the total weight of the inner phase.

33. A method of preparing a sunscreen emulsion composition that is substantially free of emulsifying agent, comprising:
   combining a sunscreen and at least one co-solvent to form a mixture;
   forming an emulsion having an inner discontinuous phase and an outer continuous phase;
   introducing the mixture into the emulsion; and
   rendering the emulsion meta-stable.

34. The method of claim 33, wherein the emulsion has a plurality of droplets of multimodal droplet size distribution.

35. A stable emulsion composition, comprising:
  at least one sunscreen active;
  an inner discontinuous phase;
  an outer continuous phase;
  an emulsifier in an amount up to about 5 wt % based upon the total weight of the inner phase.

36. The composition of claim 35, wherein the emulsion has a multimodal droplet size distribution.

37. The composition of claim 35, wherein the emulsifier is selected from a group consisting of sorbitan esters, polyglycerol esters and glycerol esters, polyoxyethylene phenols, polyoxyethylene ethers, polyoxyethylene glycol esters, polyoxyethylene sorbitan esters, polyglyceryl-3-diisostearate, polyglyceryl-3-distearate, PEG-30 dipolyhydroxystearate, quaternary ammonium compounds, dimethicone copolyol, cetyl dimethicone copolyol, lecithin, alkyl polyglucosides, acrylates/$C_{10}$–$C_{30}$ alkyl acrylate copolymers, and any combinations thereof.

* * * * *